(12) United States Patent
Lee et al.

(10) Patent No.: US 8,039,671 B2
(45) Date of Patent: Oct. 18, 2011

(54) TRANSITION METAL COMPLEX, CATALYST COMPOSITION INCLUDING THE SAME AND OLEFIN POLYMER USING CATALYST COMPOSITION

(75) Inventors: Choong Hoon Lee, Daejeon (KR); Eun Jung Lee, Daejeon (KR); Seungwhan Jung, Suwon (KR); Boram Lee, Seoul (KR); Jung A Lee, Daejeon (KR); Bun Yeoul Lee, Suwon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 13/041,526

(22) Filed: Mar. 7, 2011

(65) Prior Publication Data

US 2011/0152529 A1 Jun. 23, 2011

Related U.S. Application Data

(62) Division of application No. 11/689,917, filed on Mar. 22, 2007, now Pat. No. 7,928,256.

(30) Foreign Application Priority Data

Mar. 24, 2006 (KR) ........................ 10-2006-0026992

(51) Int. Cl.
*C07C 211/44* (2006.01)
*C07C 211/48* (2006.01)
(52) U.S. Cl. ...................................... 564/305; 564/307
(58) Field of Classification Search .................. 564/305, 564/307
See application file for complete search history.

(56) References Cited

U.S. PATENT DOCUMENTS

| 5,064,802 | A | 11/1991 | Stevens et al. |
| 6,548,686 | B2 | 4/2003 | Nabika et al. |

FOREIGN PATENT DOCUMENTS

| JP | 2002080517 | | 3/2002 |
| WO | 2007007992 | A1 | 1/2007 |

OTHER PUBLICATIONS

"Advances in Non-Metallocene Olefin Polymerization Catalysis";Vernon C. Gibson and Stefan K. Spitzmesser; Chem. Rev. 2003, 103, 283-315.

"A Novel Phenolate "Constrained Geometry" Catalyst System. Efficient Synthesis, Structural Characterization, and a-Olefin Polymerization Catalysis"; You-Xian Chen, Peng-Fei Fu, Charolette L. Stern and Tobin J. Marks; Organometallics 1997.16.5958-5963.
"Constrained Geometry Tetramethylcyclopentadienyl-phenoxytitanium Dichlorides: Template Synthesis, Structures and Catalytic Properties for Ethylene Polymerization"; Yuetao Zhang, Ying Mu, Chunsheng Lu, Guanghua Li, Jiansheng Xu, Yanrong Zhang, Dongsheng Zhu, and Shouhua Feng; Organometallics 2004. 23.540-546.
"Facile resolution of constrained geometry indenyl-phenoxide ligation", Luke E. Turner, Matthew G. Thorn, Phillip E. Fanwick and Ian P. Rothwell; Chem.Commun.2003.1034-1035.
Titanium Hydrocarbyl Complexes with a Linked Cyclopentadienyl-Alkoxide Ancillary Ligand; Participation of the Ligand in an Unusual Activation of a (Trimethylsilyl)methyl Group; Esther E. C. G. Gielens, Johan Y. Tiesnitsch, Bart Hessn, and Jan H. Teuben; Organometallics1998.17.1652-1654.
"Novel Routes to Bidentate Cyclopentadienyl-Alkoxide Complexes of Titanium: Synthesis of (n5-o-C5R14CHR2 CH2CR3R40)TiCl2"; Steven D.R. Christie, Kwok W.Man, and Richard J. Whitby; Organometallics1999.18.348-359.
"Synthesis and application in high -pressure polymerization of a titanium complex with a linked cyclopentadienyl-phenoxide ligand"; Alexander Rau, Stefan Schmitz, Gerhard Luft; J.Organomet.Chem. 2000, 608.71-75.
Chinese Office Action dated Aug. 28, 2009 (With English Translation).
"Synthesis of Main Group and Transition Metal Complexes withthe (8-Quinolyl) cyclopentadienyl Ligand and Their Application in the Polymerization of Ethylene"; Enders, et al.; Organmetallics, 2004, pp. 3832-3839.

*Primary Examiner* — Caixia Lu
(74) *Attorney, Agent, or Firm* — Cantor Colburn LLP

(57) ABSTRACT

Provided are a novel transition metal complex where a mono-cyclopentadienyl ligand to which an amido group is introduced is coordinated, a catalyst composition including the same, and an olefin polymer using the catalyst composition. The transition metal complex has a pentagon ring structure having an amido group connected by a phenylene bridge in which a stable bond is formed in the vicinity of a metal site, and thus, a sterically hindered monomer can easily approach the transition metal complex. By using a catalyst composition including the transition metal complex, a linear low density polyolefin copolymer having a high molecular weight and a very low density polyolefin copolymer having a density of 0.910 g/cc or less can be produced in a polymerization of monomers having large steric hindrance. Further, the reactivity for the olefin monomer having large steric hindrance is excellent.

1 Claim, No Drawings

TRANSITION METAL COMPLEX, CATALYST COMPOSITION INCLUDING THE SAME AND OLEFIN POLYMER USING CATALYST COMPOSITION

CROSS-REFERENCE TO RELATED PATENT APPLICATION

This application is a divisional application of U.S. application Ser. No. 11/689,917, filed on Mar. 22, 2007, now U.S. Pat. No. 7,928,256, which claims priority to Korean Patent Application No. 10-2006-0026992, filed on Mar. 24, 2006, and all the benefits accruing therefrom under 35 U.S.C. §119, the contents of which in its entirety are herein incorporated by reference.

BACKGROUND OF THE INVENTION

1. Field of the Invention

The present invention relates to a novel transition metal complex where a monocyclopentadienyl ligand to which an amido group is introduced is coordinated, a catalyst composition including the same, and an olefin polymer using the catalyst composition, and more particularly, to a novel transition metal complex containing a phenylene bridge, a catalyst composition including the same, and an olefin polymer using the catalyst composition.

2. Description of the Related Art

In the early 1990s, Dow Chemical Co. developed Me$_2$Si(Me$_4$C$_5$)(NtBu)TiCl$_2$ (Constrained-Geometry Catalyst, hereinafter referred to as CGC) (U.S. Pat. No. 5,064,802). CGC shows excellent properties in a copolymerization reaction of ethylene and α-olefin, compared to conventional metallocene catalysts. For example, (1) CGC can be used to form high molecular weight polymers due to its high reactivity at high polymerization temperature, and (2) CGC can be used for copolymerization of α-olefin having large steric hindrance, such as 1-hexene and 1-octene. Due to many useful properties, in addition to these properties described above, obtained from use of CGC, research into synthesis of CGC derivatives as a polymerization catalyst is substantially increasing in academic and industrial fields.

For example, synthesis of metal complexes comprising other various bridges instead of a silicon bridge and containing a nitrogen substituent, and polymerization using these metal complexes were performed. Examples of such metal compounds include Complexes 1 through 4 (*Chem. Rev.* 2003, 103, 283).

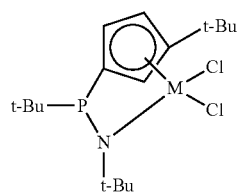

(1)

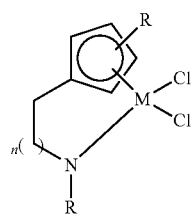

(2)

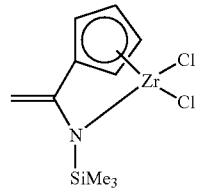

(3)

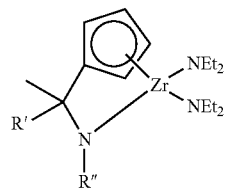

(4)

Complexes 1 through 4 respectively contain a phosphorus bridge, an ethylene or propylene bridge, a methyllidene bridge, and a methylene bridge, instead of the silicon bridge of the CGC structure. However, these complexes show low activity or poor copolymerization performance when ethylene is polymerized or when ethylene and α-olefin are copolymerized, compared to CGC.

In addition, the amino ligand in CGC can be replaced with an oxido ligand. Some of such complexes were used for polymerization. Examples of such complexes include the following Formulae.

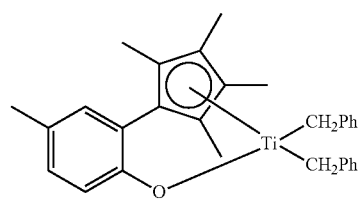

(5)

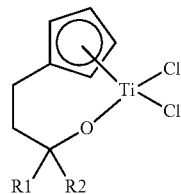

(6)

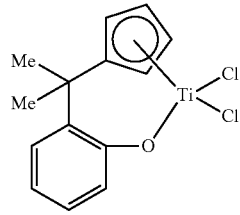

(7)

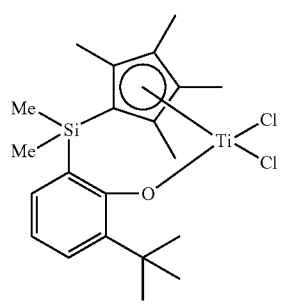

(8)

In Complex 5, which was developed by T. J. Marks et al., a cyclopentadiene (Cp) derivative is bridged to an oxido ligand by ortho-phenylene group (*Organometallics* 1997, 16, 5958). A complex having the same bridge and polymerization using the complex were suggested by Mu et al. (*Organometallics* 2004, 23, 540). A complex in which an indenyl ligand is bridged to an oxido ligand by an ortho-phenylene group was developed by Rothwell et al. (*Chem. Commun.* 2003, 1034). In Complex 6, which was developed by Whitby et al., a cyclopentadienyl ligand is bridged to an oxido ligand by three carbon atoms (*Organometallics* 1999, 18, 348). It was reported that Complex 6 showed reactivity in syndiotactic polystylene polymerization. Similar complexes to Complex 6 were developed by Hessen et al. (*Organometallics* 1998, 17, 1652). Complex 7, which was developed by Rau et al., showed reactivity when being used for ethylene polymerization and ethylene/1-hexene copolymerization at high temperature and high pressure (210□, 150 Mpa) (*J. Organomet. Chem.* 2000, 608, 71). Complex 8, which has a similar structure to Complex 7 and was developed by Sumitomo Co. (U.S. Pat. No. 6,548,686), can be used for high temperature and high pressure polymerization.

However, only some of these catalysts described above are used commercially. Accordingly, there is still a need to develop a catalyst inducing high polymerization performance.

SUMMARY OF THE INVENTION

The present invention provides a novel transition metal complex having a phenylene bridge.

The present invention also provides a novel organic amine-based compound.

The present invention also provides a catalyst composition including the transition metal complex.

The present invention also provides a method of preparing the catalyst composition.

The present invention also provides a method of preparing an olefin polymer using the catalyst composition.

The present invention also provides an olefin polymer prepared using the method.

According to an aspect of the present invention, there is provided a transition metal complex represented by Formula 1 below.

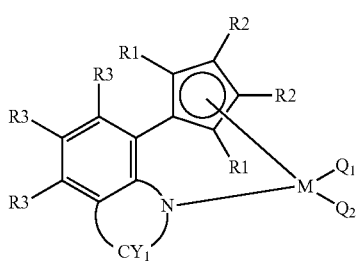

Formula 1

Here, $R_1$s and $R_2$s are each independently a hydrogen atom; a $C_{1-20}$ alkyl, $C_{6-20}$ aryl or silyl radical; a $C_{2-20}$ alkenyl, $C_{7-20}$ alkylaryl, or $C_{7-20}$ arylalkyl radical; or a metalloid radical of Group 14 substituted with a $C_{1-20}$ hydrocarbyl, wherein $R_1$ and $R_2$ can be connected to each other by an alkylidine radical containing a $C_{1-20}$ alkyl or aryl radical to form a ring;

each of the $R_3$s are independently a hydrogen atom; or a halogen radical; or a $C_{1-20}$ alkyl, $C_{6-20}$ aryl, $C_{1-20}$ alkoxy, $C_{6-20}$ aryloxy, or amido radical, wherein at least two $R_3$'s can be connected to each other to form an aliphatic or aromatic ring;

CY1 is a substituted or unsubstituted aliphatic or aromatic ring;

M is a Group 4 transition metal; and $Q_1$ and $Q_2$ are each independently a halogen radical; a $C_{1-20}$ alkylamido, or $C_{6-20}$ arylamido radical; a $C_{1-20}$ alkyl, $C_{2-20}$ alkenyl, $C_{6-20}$ aryl, $C_{7-20}$ alkylaryl, or $C_{7-20}$ arylalkyl radical; or a $C_{1-20}$ alkylidene radical.

The transition metal complex represented by Formula 1 may be represented by Formula 2 below.

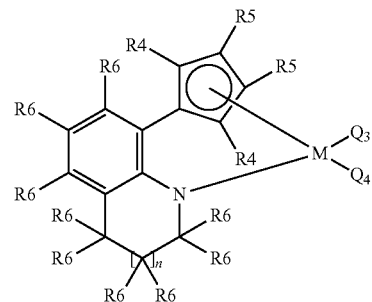

Formula 2

Here, $R_4$s and $R_5$s are each independently a hydrogen atom; or a $C_{1-20}$ alkyl, $C_{6-20}$ aryl or silyl radical;

each of the $R_6$s are each independently a hydrogen atom; or a $C_{1-20}$ alkyl or $C_{6-20}$ aryl radical; a $C_{2-20}$ alkenyl, $C_{7-20}$ alkylaryl or $C_{7-20}$ arylalkyl radical; or a $C_{1-20}$ alkoxyl, $C_{6-20}$ aryloxyl or amido radical, wherein at least two $R_6$'s can be connected to each other to form an aliphatic or aromatic ring;

$Q_3$ and $Q_4$ are each independently a halogen radical; a $C_{1-20}$ alkylamido or $C_{6-20}$ arylamido radical; or a $C_{1-20}$ alkyl radical; n is a integer such as 0 or 1; and M is a Group 4 transition metal.

The transition metal complex represented by Formula 1 may be represented by one of the following Formulae.

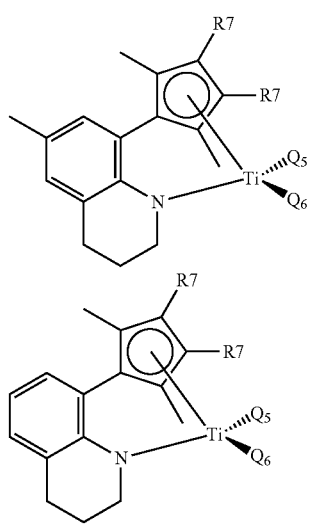

-continued
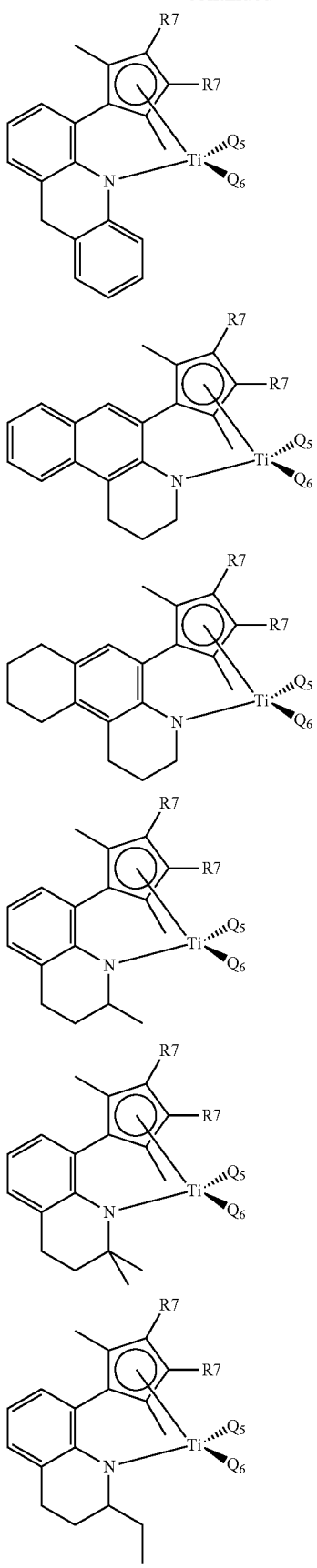
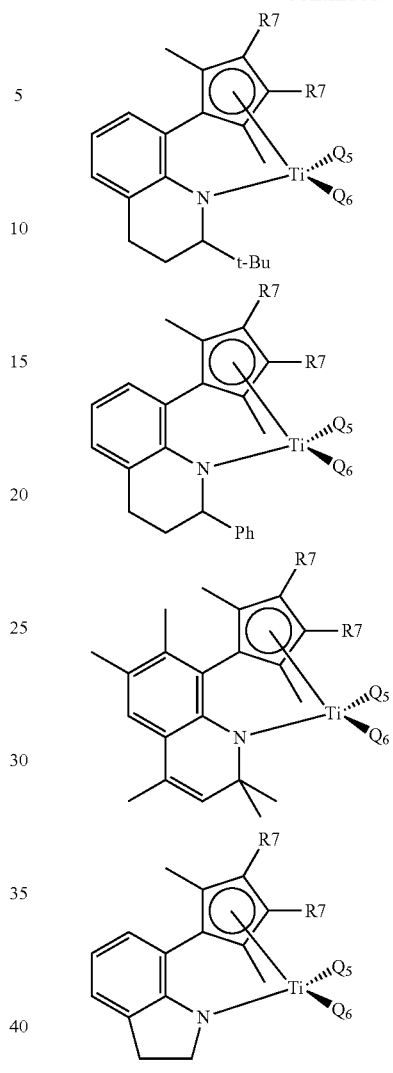
Here, each of the R$_7$s are independently a hydrogen atom or a methyl radical, and
Q$_5$ and Q$_6$ are each independently a methyl, dimethylamido or chloride radical.
According to another aspect of the present invention, there is provided an amine-based compound represented by Formulae 3 and 4 below.
Formula 3
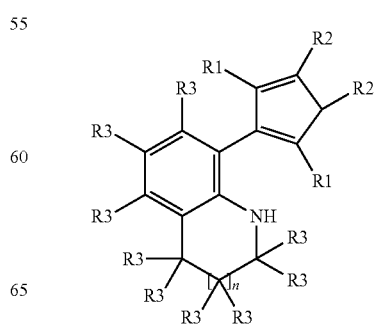

Formula 4

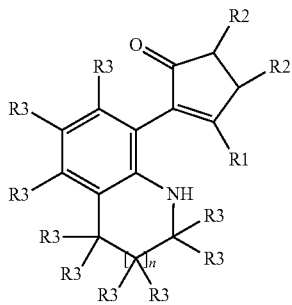

Here, $R_1$, $R_2$ and $R_3$ are described above. And n is a integer such as 0 or 1.

According to another aspect of the present invention, there is provided a catalyst composition including: a transition metal complex represented by Formula 1; and at least one cocatalyst compound selected from the group consisting of compounds represented by Formulae 5, 6, and 7 below.

Formula 1

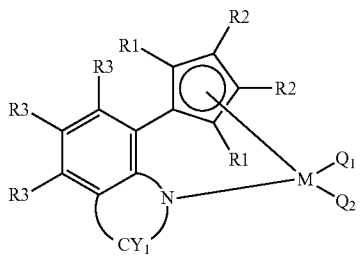

Here, CY1, $R_1$, $R_2$, $R_3$, $Q_1$ and $Q_2$ are described above.

—[Al($R_8$)—O]$_a$—  Formula 5

Here, each of the $R_8$s are independently a halogen radical; a $C_{1-20}$ hydrocarbyl radical; and a $C_{1-20}$ hydrocarbyl radical substituted with a halogen atom, or a is an integer of 2 or greater.

D($R_8$)$_3$  Formula 6

Here, D is aluminum or boron, and $R_8$ is described above.

[L-H]$^+$[Z(A)$_4$]$^-$ or [L]$^+$[Z(A)$_4$]$^-$  Formula 7

Here, L is a neutral or cationic Lewis acid; H is a hydrogen atom; Z is a Group 13 atom; and each of the As are independently a $C_{6-20}$ aryl or $C_{1-20}$ alkyl radical in which at least one hydrogen atom is substituted with a halogen atom, or a $C_{1-20}$ hydrocarbyl, $C_{1-20}$ alkoxy, or phenoxy radical.

The transition metal complex represented by Formula 1 of the catalyst composition may be one of compounds represented by the following Formulae.

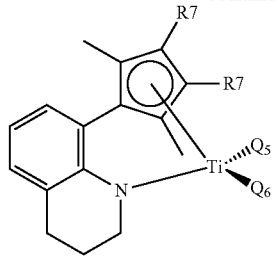

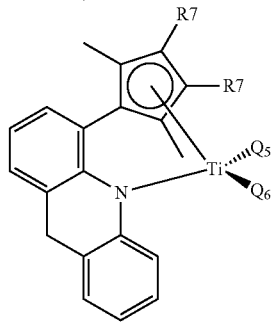

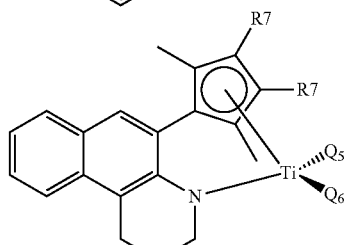

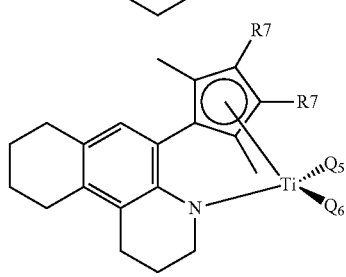

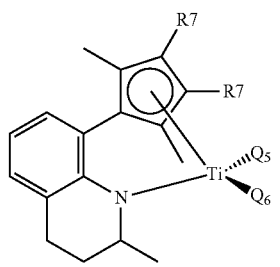

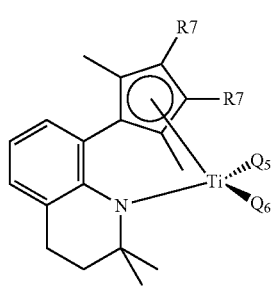

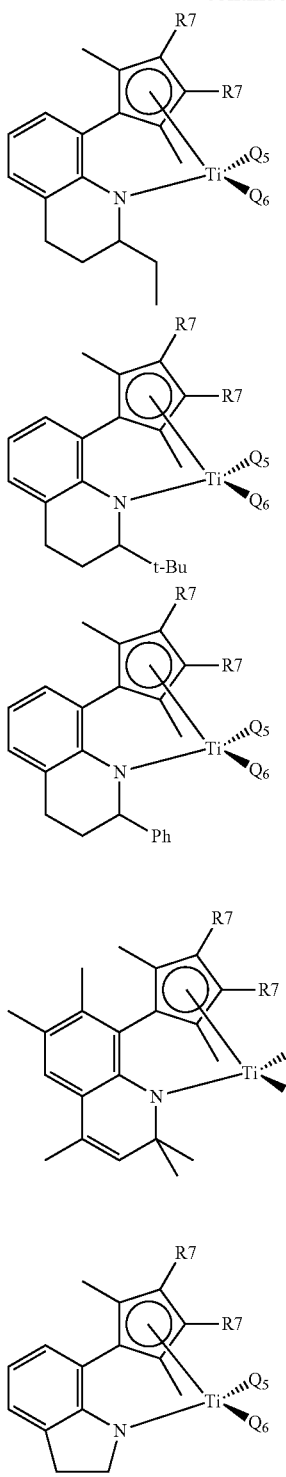

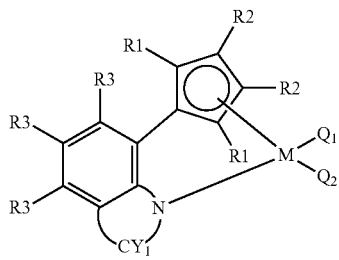

$$-[Al(R_8)-O]_a- \quad \text{Formula 5}$$

$$D(R_8)_3 \quad \text{Formula 6}$$

$$[L-H]^+[ZA_4]^- \text{ or } [L]^+[ZA_4]^- \quad \text{Formula 7}$$

Here, CY1, $R_1$, $R_2$, $R_3$, $R_8$, $Q_1$, $Q_2$, a, D, L, H, Z and A are described above.

The transition metal complex represented by Formula 1 in the method of preparing the catalyst composition may be one of compounds represented by the following Formulae.

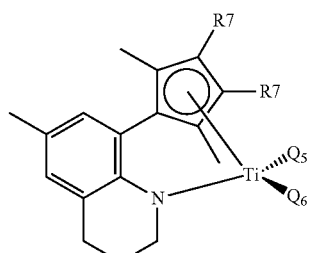

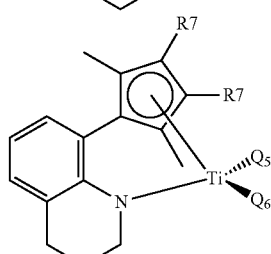

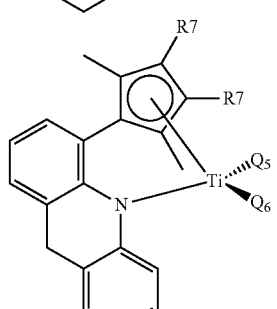

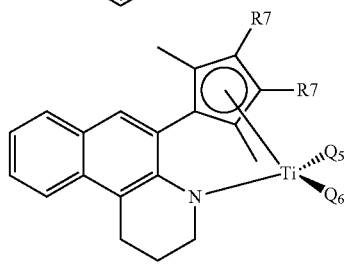

Here, $R_7$, $Q_5$ and $Q_6$ are described above.

According to another aspect of the present invention, there is provided a method of preparing a catalyst composition including: bringing the transition metal complex represented by Formula 1 below into contact with a compound represented by Formula 5 or 6 below to obtain a mixture; and adding a compound represented by Formula 7 below to the mixture.

-continued

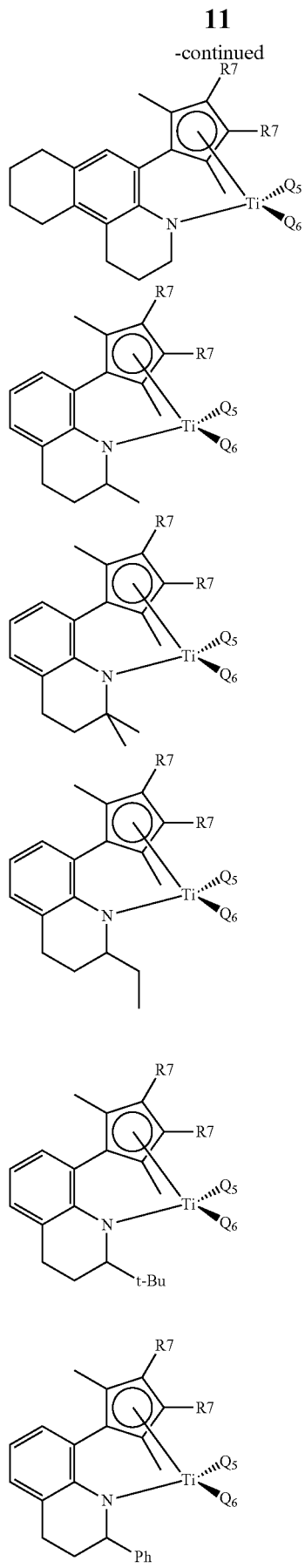

-continued

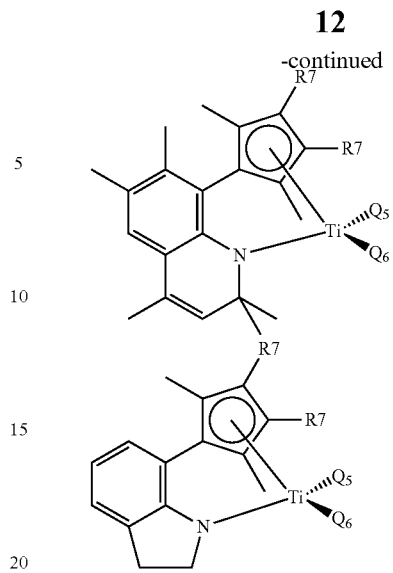

Here, $R_7$, $Q_5$ and $Q_6$ are described above.

The molar ratio of the transition metal complex to the compound represented by Formula 5 or 6 may be in the range of 1:2 to 1:5000, and the molar ratio of the transition metal complex to the compound represented by Formula 7 may be in the range of 1:1 to 1:25.

According to another aspect of the present invention, there is provided a method of synthesizing an olefin polymer, wherein the catalyst composition is brought into contact with a monomer.

The monomer may be at least one monomer selected from the group consisting of ethylene, propylene, 1-butene, 1-pentene, 4-methyl-1-pentene, 1-hexene, 1-heptene, 1-octene, 1-decene, 1-undecene 1-dodecene, 1-tetradecene, 1-hexadecene and 1-eicosene.

According to another aspect of the present invention, there is provided an olefin polymer synthesized using the method of synthesizing an olefin polymer.

The monomer that is used to synthesize the olefin polymer may include: ethylene; and at least one comonomer selected from the group consisting of propylene, 1-butene, 1-hexene, 4-methyl-1-pentene, and 1-octene.

A transition metal complex according to an embodiment of the present invention has an amido group connected by a phenylene bridge, so that a sterically hindered monomer easily approaches the transition metal complex and a pentagon ring structure of the transition metal complex is stably maintained, compared to a conventional transition metal complex having a silicon bridge and an oxido ligand. By using a catalyst composition including the transition metal complex according to an embodiment of the present invention, a polyolefin copolymer having a very low density less than 0.910 g/cc can be obtained.

DETAILED DESCRIPTION OF THE INVENTION

Hereinafter, the present invention will be described in detail by explaining embodiments of the invention. The invention may, however, be embodied in many different forms and should not be construed as being limited to the embodiments set forth herein; rather, these embodiments are provided so that this disclosure will be thorough and complete, and will fully convey the concept of the invention to those skilled in the art.

A transition metal complex according to an embodiment of the present invention may be represented by Formula 1 below.

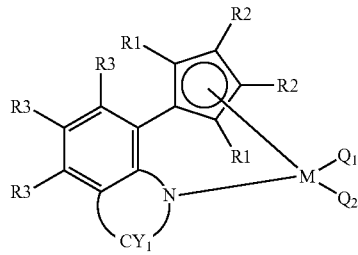

Formula 1

Here, $R_1$s and $R_2$s are each independently a hydrogen atom; a $C_{1-20}$ alkyl, $C_{6-20}$ aryl or silyl radical; a $C_{2-20}$ alkenyl, $C_{7-20}$ alkylaryl, or $C_{7-20}$ arylalkyl radical; or a metalloid radical of Group 14 substituted with a $C_{1-20}$ hydrocarbyl, wherein $R_1$ and $R_2$ can be connected to each other by an alkylidine radical containing a $C_{1-20}$ alkyl or aryl radical to form a ring;

each of the $R_3$s are independently a hydrogen atom; a halogen radical; or a $C_{1-20}$ alkyl, $C_{6-20}$ aryl, $C_{1-20}$ alkoxy, $C_{6-20}$ aryloxy, or amido radical, wherein at least two $R_3$s can be connected to each other to form an aliphatic or aromatic ring;

CY1 is a substituted or unsubstituted aliphatic or aromatic ring;

M is a Group 4 transition metal; and $Q_1$ and $Q_2$ are each independently a halogen radical; a $C_{1-20}$ alkylamido, or $C_{6-20}$ arylamido radical; a $C_{1-20}$ alkyl, $C_{2-20}$ alkenyl, $C_{6-20}$ aryl, $C_{7-20}$ alkylaryl, or $C_{7-20}$ arylalkyl radical; and a $C_{1-20}$ alkylidene radical.

A metal site of the transition metal complex represented by Formula 1 according to the current embodiment of the present invention is connected to a cyclopentadienyl ligand which is connected to a phenylene bridge to which a ring shaped amido group is introduced. Thus, by its structural inherence the angle of Cp-M-N structure tends to be narrow, and a wide angle tends to be maintained in the $Q_1$-M-$Q_2$ structure to which a monomer approaches. In addition, compared to a CGC structure that includes a silicon bridge, the transition metal complex represented by Formula 1 has a stable and strong ring in which Cp, a phenylene bridge, nitrogen, and a metal site forms a pentagon structure. That is, a securer complex compound structure can be obtained since the nitrogen atom in the amido group is cyclically connected to the phenylene bridge through two bonds. Accordingly, when the complex compound which is activated by a cocatalyst such as methylaluminoxane or $B(C_6F_5)_3$, is applied to the synthesis of polyolefin, a polyolefin which has a high activity, a high molecular weight, and a high degree of copolymerization can be obtained even at a high reaction temperature. In particular, a very low density polyolefin copolymer having a density of 0.910 g/cc or less as well as 0.910~0.930 g/cc can also be prepared since the structure of the catalyst can contain a great amount of α-olefin. Various substituents can be included in a cyclopentadienyl ring and a quinoline-based ring. Thus, the structures and properties of the polyolefin can be controlled since electronic and steric environments in the vicinity of the metal can be easily controlled. The transition metal complex according to the current embodiment of the present invention may be used to prepare a catalyst that is used to polymerize olefin monomers. However, use of the transition metal complex is not limited thereto.

The transition metal complex represented by Formula 1 may have a structure represented by Formula 2. The compound represented by Formula 2 can control electronic and steric environments in the vicinity of metal.

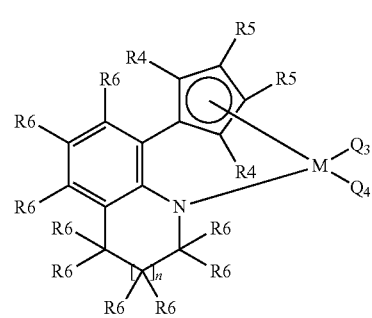

Formula 2

Here, $R_4$s and $R_5$s are each independently a hydrogen atom; and a $C_{1-20}$ alkyl, $C_{6-20}$ aryl or silyl radical;

each of the $R_6$s are independently a hydrogen atom; a $C_{1-20}$ alkyl or $C_{6-20}$ aryl radical; a $C_{2-20}$ alkenyl, $C_{7-20}$ alkylaryl or $C_{7-20}$ arylalkyl radical; and a $C_{1-20}$ alkoxyl, $C_{6-20}$ aryloxyl or amido radical, wherein at least two $R_6$s can be connected to each other to form an aliphatic or aromatic ring;

$Q_3$ and $Q_4$ are each independently a halogen radical; a $C_{1-20}$ alkylamido or $C_{6-20}$ arylamido radical; and a $C_{1-20}$ alkyl radical; n is a integer such as 0 or 1; and M is a Group 4 transition metal.

The transition metal complex represented by Formula 1 or 2 may be one of the compounds represented by the following Formulae. These compounds can control electronic and steric environments in the vicinity of metal.

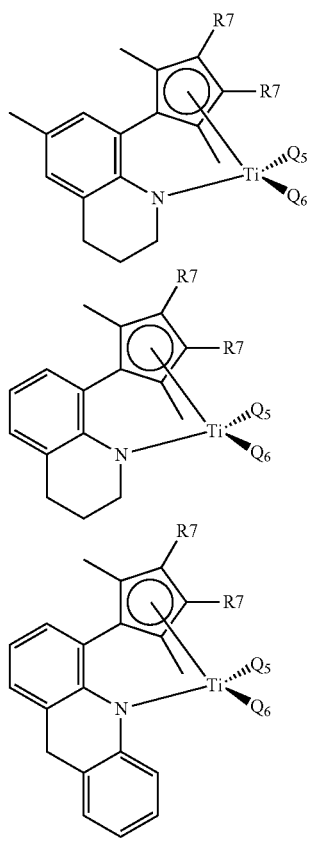

-continued

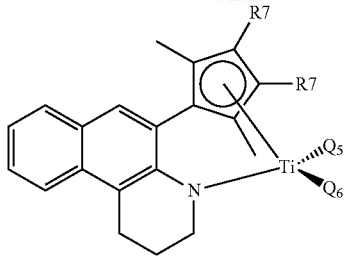

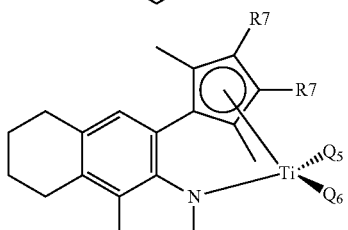

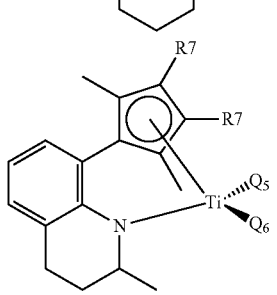

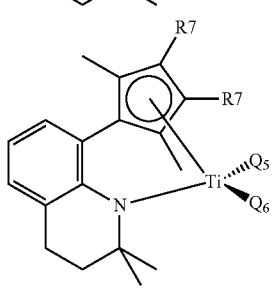

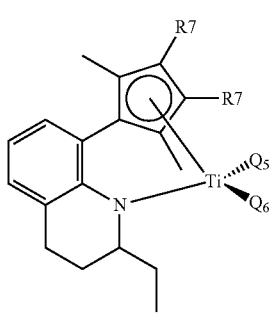

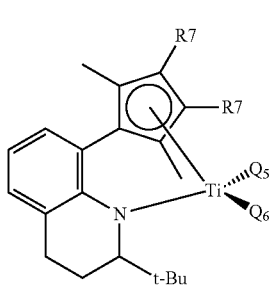

-continued

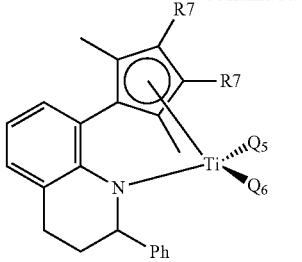

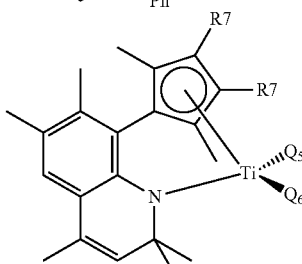

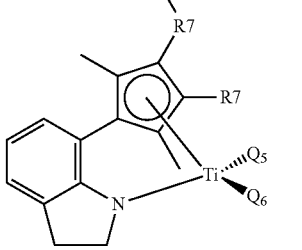

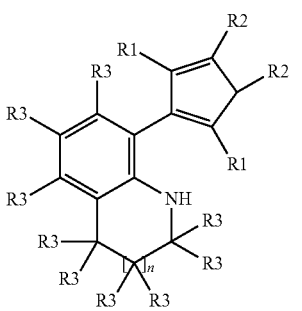

Here, each of the $R_7$s are independently a hydrogen atom or a methyl radical, and $Q_5$ and $Q_6$ are each independently a methyl, dimethylamido or chloride radical.

According to another embodiment of the present invention, there is provided an amine-based compound represented by Formulae 3 and 4 below as a ligand of the transition metal complex of Formula 1 or 2.

Formula 3

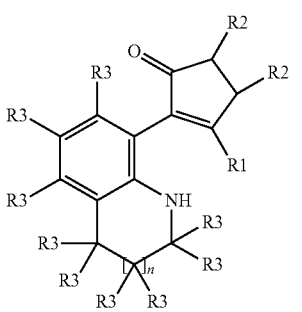

Formula 4

Here, $R_1$, $R_2$ and $R_3$ are as described above.
And, n is a integer such as 0 or 1.

When these ligands are coordinated with metal, a phenylene bridge is formed, and nitrogen and cyclopentadiene are coordinated with metal. These compounds may be used as ligands of the transition metal complex. However, use of the compounds is not limited thereto. That is the compounds can be used in any applications.

According to an embodiment of the present invention, there is provided a catalyst composition including: a transition metal complex represented by Formula 1 or 2; and at least one cocatalyst compound selected from the group consisting of compounds represented by Formulae 5, 6, and 7 below.

The catalyst composition may be used for homopolymerization or copolymerization of olefin.

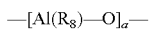     Formula 5

Here, each of the $R_8$s are independently a halogen radical; a $C_{1-20}$ hydrocarbyl radical; or a $C_{1-20}$ hydrocarbyl radical substituted with a halogen atom, and a is an integer of 2 or greater.

     Formula 6

Here, D is aluminum or boron, and $R_8$ is as described above.

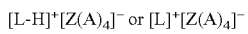     Formula 7

Here, L is a neutral or cationic Lewis acid; H is a hydrogen atom; Z is a Group 13 atom; and each of the As are independently a $C_{6-20}$ aryl or $C_{1-20}$ alkyl radical in which at least one hydrogen atom is substituted with a halogen atom, or a $C_{1-20}$ hydrocarbyl, $C_{1-20}$ alkoxy, or phenoxy radical.

The transition metal complex represented by Formula 1 of the catalyst composition may be one of the compounds represented by the following Formulae.

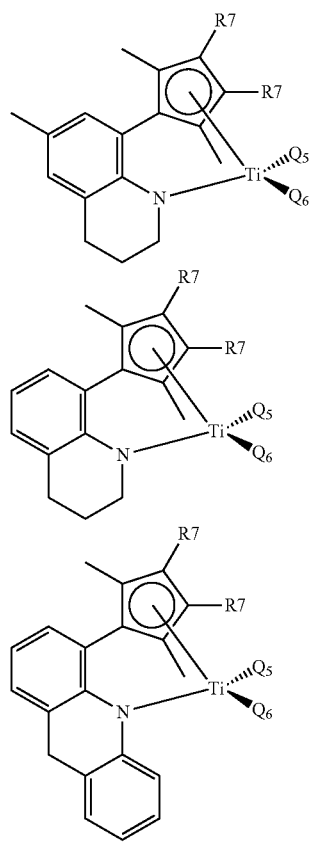

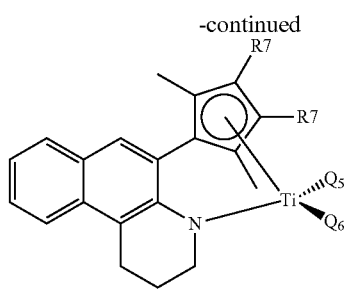

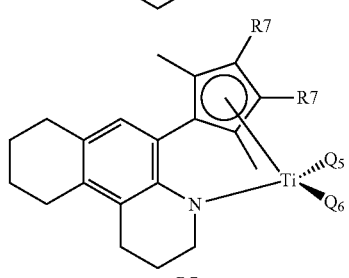

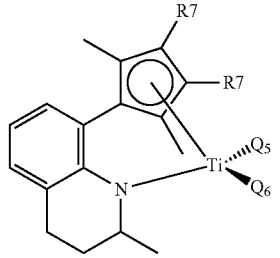

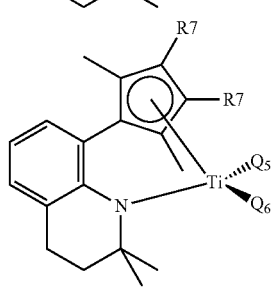

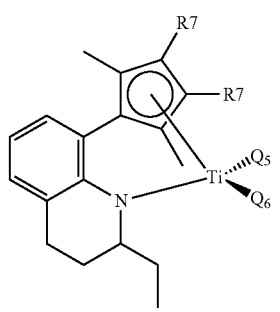

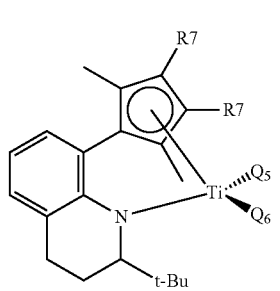

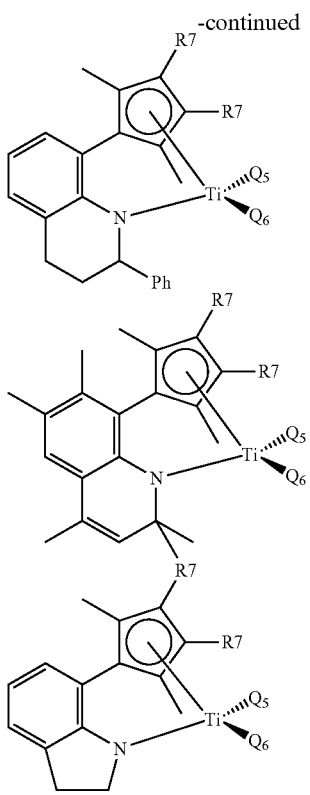

Here, each of the $R_7$s are independently a hydrogen atom or a metal radical, and $Q_5$ and $Q_6$ are each independently a methyl, dimethylamido or chloride radical.

A method of preparing the catalyst composition according to an embodiment of the present invention includes: bringing the transition metal complex represented by Formula 1 into contact with a compound represented by Formula 5 or 6 to obtain a mixture; and adding a compound represented by Formula 7 to the mixture.

A method of preparing the catalyst composition according to another embodiment of the present invention includes bringing the transition metal complex represented by Formula 1 into contact with a compound represented by Formula 7.

In the former method, the molar ratio of the transition metal complex to the compound represented by Formula 5 or 6 may be in the range of 1:2 to 1:5,000, more preferably in the range of 1:10 to 1:1,000, and most preferably in the range of 1:20 to 1:500.

Meanwhile, the molar ratio of the transition metal complex to the compound represented by Formula 7 may be in the range of 1:1 to 1:25, more preferably in the range of 1:1 to 1:10, and most preferably in the range of 1:1 to 1:5.

When the molar ratio of the transition metal complex to the compound represented by Formula 5 or 6 is less than 1:2, the metal compound is insufficiently alkylated since the amount of an alkylating agent is too small. On the other hand, when the molar ratio of the transition metal complex to the compound represented by Formula 5 or 6 is greater than 1:5,000, the metal compound is alkylated, but excess alkylating agent can react with the activator of Formula 7 so that the alkylated metal compound is less activated. When the molar ratio of the transition metal complex to the compound represented by Formula 7 is less than 1:1, the amount of the activator is relatively small so that the metal compound is less activated. On the other hand, when the molar ratio of the transition metal complex to the compound represented by Formula 7 is greater than 1:25, the metal compound may be completely activated but excess activator remains, that is, the preparation process for the catalyst composition is expensive, and the obtained polymer purity is poor.

In the latter method, the molar ratio of the transition metal complex to the compound represented by Formula 7 may be in the range of 1:10 to 1:10,000, more preferably in the range of 1:100 to 1:5,000, and most preferably in the range of 1:500 to 1:2,000. When the molar ratio of the transition metal complex to the compound represented by Formula 7 is less than 1:10, the metal compound is insufficiently alkylated since the amount of an alkylating agent is relatively small. On the other hand, when the molar ratio of the transition metal complex to the compound represented by Formula 7 is greater than 1:10,000, the metal compound may be completely activated but excess activator remains, that is, the preparation process for the catalyst composition is expensive, and the obtained polymer purity is poor.

A reaction solvent used in the preparation of the activated catalyst composition may be a hydrocarbon solvent such as pentane, hexane, or heptane, or an aromatic solvent such as benzene and toluene, but is not limited thereto and any solvent that is used in the art can be used.

In addition, the transition metal complex represented by Formula 1 or 2 and the cocatalyst may be loaded on silica or alumina.

The compound represented by Formula 5 may be an alkylaluminoxane, more preferably one of methylaluminoxane, ethylaluminoxane, isobutylaluminoxane, and butylaluminoxane, and most preferably methylaluminoxane.

The compound represented by Formula 6 may be one of trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, dripropylboron, and tributylboron, and more preferably trimethylaluminum, triethylaluminum, or triisobutylaluminum, but is not limited thereto.

Examples of the compound represented by Formula 7 may include triethylammoniumtetraphenylboron, tributylammoniumtetraphenylboron, trimethylammoniumtetraphenylboron, tripropylammoniumtetraphenylboron, trimethylammoniumtetra(p-tolyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylanilinium tetraphenylboron, N,N-diethylanilinium tetraphenylboron, N,N-diethylanilinium tetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra (p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentatetraphenylaluminum, triphenylphosphoniumtetraphenylaluminum, trimethylphosphoniumtetraphenylaluminum, triethylammoniumtetraphenylaluminum, tributylammoniumtetraphenylaluminum, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, triphenylcarboniumtetra(p-trifluoromethylphenyl)boron, and triphenylcarboniumtetrapentafluorophenylboron.

According to an embodiment of the present invention, there is provided a method of synthesizing an olefin polymer using the catalyst composition.

In the method, the catalyst composition including a transition metal complex represented by Formula 1 or 2 and at least one compound selected from the group consisting of compounds represented by Formulae 5, 6, and 7 is brought into contact with an olefin-based monomer to prepare a polyolefin homopolymer or copolymer.

The transition metal complex that is used in the method of preparing the homopolymer or copolymer may be represented by one of the following Formulae.

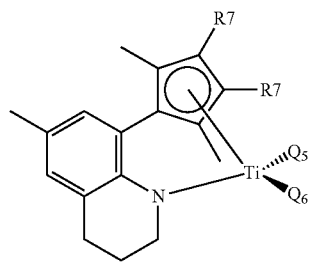

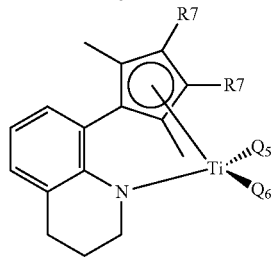

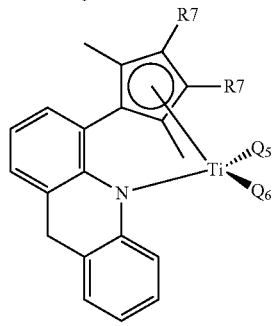

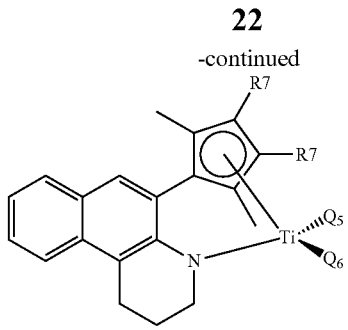

-continued

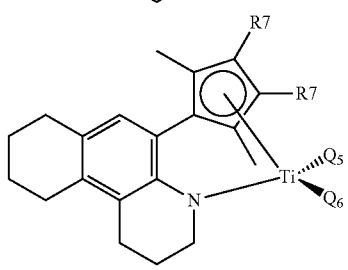

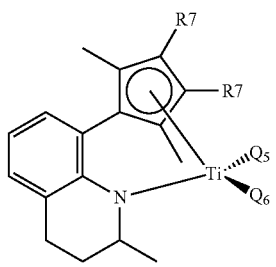

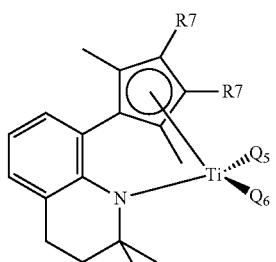

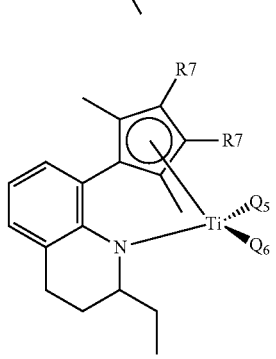

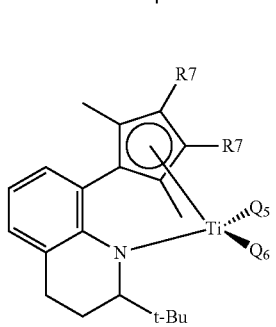

-continued

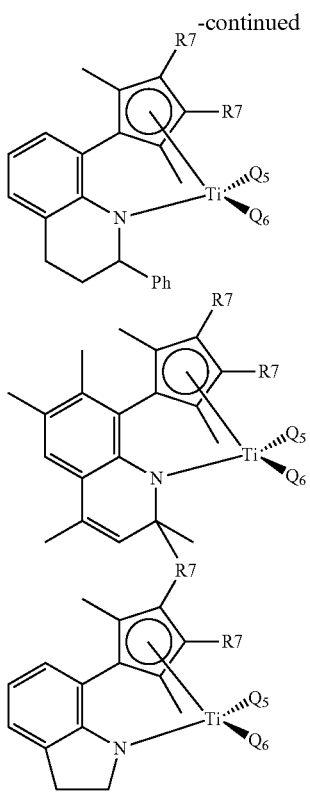

Here, each of the R₇s are independently a hydrogen atom or a methyl radical, and Q₅ and Q₆ are each independently a methyl, dimethylamido or chloride radical.

A polymerization process using the catalyst composition may be a solution process, but when the catalyst composition is used together with an inorganic support, such as silica, the polymerization process can also be a slurry or gas phase process.

In the method, the catalyst composition may be dissolved or diluted in a solvent suitable for olefin polymerization, before being used. Examples of the solvent may include a $C_{5-12}$ aliphatic hydrocarbon solvent such as pentane, hexane, heptane, nonane, decane, and derivatives thereof; an aromatic hydrocarbon solvent such as toluene or benzene; and a hydrocarbon solvent substituted with a chlorine atom such as dichloromethaneor chlorobenzene. The solvent may be treated with a small amount of alkylaluminum to eliminate a small amount of water and air which poison the catalyst composition, or a cocatalyst can further be used.

Examples of the olefin-based monomer which is polymerized using the metal complexes and the cocatalysts may include α-olefin and a cyclic olefin. A diene olefin-based monomer or a triene olefin-based monomer which have at least two double bonds may also be polymerized. Examples of the olefin-based monomer or triene olefin-based monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene and 1-eicosene, norbornene, norbornadiene, ethylidene norbornene, phenylnorbornene, vinyl norbornene, dicyclopentadiene, 1,4-butadiene, 1,5-pentadiene, 1,6-hexadiene, styrene, α-methylstyrene, divinylbenzene, and 3-chloromethyl styrene. More than two of the monomers may be mixed and copolymerized.

In particular, the catalyst composition according to an embodiment of the present invention is used to copolymerize ethylene and 1-octene having large steric hindrance at a high reaction temperature of 90° C. or higher to thereby obtain a copolymer having high molecular weight but having a very low density less than 0.910 g/cc.

According to an embodiment of the present invention, there is provided an olefin polymer prepared using a method of synthesizing an olefin The olefin polymer may be a homopolymer or a copolymer. When the olefin polymer is a copolymer of ethylene and a comonomer, the monomer may be at least one copolymer selected from the group consisting of ethylene, propylene, 1-butene, 1-hexene, 4-methyl-1-pentene, and 1-octene.

The present invention will be described in greater detail with reference to the following examples. The following examples are for illustrative purposes only and are not intended to limit the scope of the invention.

Synthesis of Ligands and Transition Metal Complexes

Organic reagents and solvents were obtained from Aldrich Co., Inc. and Merck Co., Inc. and purified using a standard method. Each process for the synthesis was performed while isolated from air and moisture to improve reproducibility of experiments. The structure of compounds produced in the following examples was identified using a 400 MHz nuclear magnetic resonance (NMR) and an X-ray spectrometer.

Example 1

5-bromo-7-methyl-1,2,3,4-tetrahydroquinoline 1.16 g (7.90 mmol) of 6-methyl-1,2,3,4-tetrahydroquinoline was dissolved in 4 ml of carbon tetrachloride and the solution was cooled to −20° C. 1.41 g (7.90 mml) of solid-state N-bromosuccinimide was slowly added to the solution and the resultant mixture was reacted at room temperature for 5 hours. The product was filtered using a column chromatography with a MC/hexane (v:v=1:1) solvent, and 0.71 g of pale yellow oil was obtained (40%).

$^1$H NMR ($C_6D_6$): δ 1.42-1.52 (m, 2H, $CH_2$), 2.00 (s, 3H, $CH_3$), 2.39 (t, J=6.4 Hz, 2H, $CH_2$), 2.75 (dt, J=2.8, 8.4 Hz, 2H, N—$CH_2$), 4.04 (br s, 1H, NH), 6.51 (s, 1H, $C_6H_2$), 7.09 (s, 1H, $C_6H_2$) ppm. $^{13}$C{$^1$H} NMR ($C_6D_6$): δ 20.06, 22.04, 27.60, 41.91, 108.84, 122.59, 126.16, 129.48, 130.67, 139.79 ppm. Anal. Calc. ($C_{10}H_{12}BrN$): C, 53.12; H, 5.35; N, 6.19%. Found: C, 53.30; H, 5.13; N, 6.51%.

Example 2

5-(3,4-dimethyl-2-cyclopentene-1-one)-7-methyl-1,2,3,4-tetrahydroquinoline 1.27 g (8.26 mmol) of 2-(dihydroxyboryl)-3,4-dimethyl-2-cyclopentene-1-one, 1.25 g (11.8 mmol) of $Na_2CO_3$, 0.182 g (0.157 mmol) of $Pd(PPh_3)_4$, (Ph: phenyl group) and 7.87 mmol of 5-bromo-7-methyl-1,2,3,4-tetrahydroquinoline were mixed. 21 ml of degassed dimethylether (DME) and 7 ml of distilled water were added to the mixture. The resultant mixture was heated at 95° C. overnight. The reaction mixture was cooled to room temperature, and about twice extracted with 50 ml of ethylacetate. The product was filtered using a column chromatography with a hexane/ethylacetate (v:v=2:1) solvent, and a pale yellow solid product was obtained (90%).

$^1$H NMR($C_6D_6$): δ 0.77 (d, J=7.2 Hz, 3H, $CH_3$), 1.59-1.70 (m, 2H, $CH_2CH_2CH_2$), 1.65 (s, 3H, $CH_3$), 1.84 (dd, J=2.4, 18.4 Hz, 1H, $OCCH_2$), 2.21 (s, 3H, $CH_3$), 2.20-2.30 (m, 1H,

CH), 2.44 (dd, J=6.4, 18.4 Hz, 1H, OCCH$_2$), 2.60 (br t, J=6 Hz, 2H, CH$_2$), 2.97 (br t, J=5.6 Hz, 2H, N—CH$_2$), 4.06 (s, 1H, NH), 6.66 (s, 1H, CH, C$_6$H$_2$), 6.74 (s, 1H, C$_6$H$_2$) ppm. $^{13}$C{$^1$H} NMR (C$_6$D$_6$): δ 15.83, 19.06, 20.58, 22.51, 27.92, 37.52, 42.48, 43.55 ppm. Anal. Calc. (C$_{17}$H$_{21}$NO): C, 79.96; H, 8.29; N, 5.49%. Found: C, 80.17; H, 8.44; N, 5.75%.

Example 3

5-(2,3,5-trimethyl-1,3-cyclopentadienyl)-7-methyl-1,2,3,4-tetrahydroquinoline 21.4 mmol of anhydrous La(OTf)$_3$, (Tf: triflate) was mixed with 24 ml of tetrahydrofuran (THF) and the mixture was cooled to −78° C. 13.4 ml (21.4 mmol) of MeLi (Me: methyl) was added to the mixture and reacted for about 1 hour. 7.13 mmol of 5-(3,4-dimethyl-2-cyclopentene-1-one)-7-methyl-1,2,3,4-tetrahydroquinoline was added to the mixture and reacted at −78° C. for 2 hours. The resultant mixture was extracted using water and acetate. The obtained organic layer was added to 20 ml (2N) of HCl and the mixture was shaken for 2 minutes. The resultant mixture was neutralized with 20 ml of NaHCO$_3$ water solution and dried with MgSO$_4$. The product was filtered using a column chromatography with hexane/ethylacetate (v:v=10:1) solvent, and a pale yellow solid product was obtained (40%).

$^1$H NMR(C$_6$D$_6$): δ 1.66-1.71 (m, 2H, CH$_2$CH$_2$CH$_2$), 1.80 (s, 3H, CH$_3$), 1.89 (s, 3H, CH$_3$), 1.90 (s, 3H, CH$_3$), 2.24 (s, 3H, CH$_3$), 2.64 (br t, J=6.4 Hz, 2H, CH$_2$), 2.74 (d, J=2 Hz, 2H, CH$_2$), 2.86-2.92 (m, 2H, N—CH$_2$), 3.62 (br s, 1H, NH), 6.75 (s, 1H, C$_6$H$_2$), 6.77 (s, 1H, C$_6$H$_2$) ppm. $^{13}$C{$^1$H} NMR (C$_6$D$_6$): δ 11.85, 13.61, 14.39, 20.74, 22.86, 27.70, 42.20, 48.88, 120.81, 122.01, 124.78, 128.68, 129.36, 132.87, 136.36, 136.65, 140.75, 141.15 ppm.

Example 4

([(7-Methyl-1,2,3,4-tetrahydroquinolin-8-yl)trimethylcyclopentadienyl-eta5,kap a-N]titanium bis(dimethylamide)) compound 0.696 mmol of 5-(2,3,5-trimethyl-1,3-cyclopentadienyl)-7-methyl-1,2,3,4-tetrahydroquinoline ligand and 0.156 g (0.696 mmol) of Ti(NMe$_2$)$_4$ were dissolved in 2 ml of toluene. The mixture was reacted at 80° C. for two days. After the solvents were eliminated, a red solid product was obtained (100%). The obtained titanium compound was identified through $^1$H-NMR spectroscope.

$^1$H NMR (C$_6$D$_6$): δ1.69-1.74 (m, 2H, CH$_2$CH$_2$CH$_2$), 1.86 (s, 3H, CH$_3$), 1.88 (s, 3H, CH$_3$), 1.92 (s, 3H, CH$_3$), 2.31 (s, 3H, CH$_3$), 2.57 (t, J=5.6 Hz, 2H, CH$_2$), 2.95 (s, 6H, NCH$_3$), 3.27 (s, 6H, NCH$_3$), 4.02 (ddd, J=5.2, 7.2, 12.0 Hz, 1H, NCH$_2$), 4.24 (dt, J=5.2, 12.4 Hz, 1H, NCH$_2$), 5.78 (s, 1H, Cp-H), 6.77 (s, 1H, C$_6$H$_2$), 6.91 (s, 1H, C$_6$H$_2$) ppm.

Example 5

([(7-Methyl-1,2,3,4-tetrahydroquinolin-8-yl)trimethylcyclopentadienyl-eta5,kap a-N]titanium dichloride) compound 2 ml of toluene was added to the bis(dimethylamido)titanium compound that was obtained in Example 4. 0.269 g (2.09 mmol) of Me$_2$SiCl$_2$ was added to the mixture at room temperature and the mixture was reacted for about 4 hours. The obtained product was recrystallized in hexane at −30° C. and 0.183 g of a pure red solid product was obtained (66%).

$^1$H NMR (C$_6$D$_6$): δ1.36-1.44 (m, 2H, CH$_2$CH$_2$CH$_2$), 1.76 (s, 3H, CH$_3$), 1.85 (s, 3H, CH$_3$), 2.07 (s, 3H, CH$_3$), 2.18 (s, 3H, CH$_3$), 2.12 (t, J=4 Hz, 2H, CH$_2$), 4.50-4.70 (m, 2H, N—CH$_2$), 6.02 (s, 1H, Cp-H), 6.59 (s, 1H, C$_6$H$_2$), 6.78 (s, 1H, C$_6$H$_2$) ppm. $^{13}$C{$^1$H} NMR (C$_6$D$_6$): 12.76, 14.87, 15.06, 21.14, 22.39, 26.32, 54.18, 117.49, 120.40, 126.98, 129.53, 130.96, 131.05, 133.19, 143.22, 143.60, 160.82 ppm. Anal. Calc. (C$_{18}$H$_{21}$Cl$_2$NTi): C, 58.41; H, 5.72; N, 3.78%. Found: C, 58.19; H, 5.93; N, 3.89%.

Example 6

5-(tetramethyl-1,3-cyclopentadienyl)-1,2,3,4-tetrahydroquinoline 957 mg (7.185 mmol) of 1,2,3,4-tetrahydroquinoline was dissolved in 10 ml of THF, and stirred at −78° C. for 30 minutes. 2.87 ml (7.185 mmol) of nBuLi was added thereto using a syringe under a nitrogen atmosphere (yellow suspension). The mixture was sufficiently stirred for 3 hours, and the temperature was increased to −20° C. to eliminate the gas. The temperature was cooled again to −78° C. and CO$_2$ was injected to the mixture (The color of the mixture turned to colorless white). The temperature was increased to −20° C. and the remaining CO$_2$ was eliminated in vacuum for 1 hour. Then, 5.07 ml (8.622 mmol) of tert-butyllithium (BuLi) was added to the mixture (The color of the mixture turned to red). While the temperature was maintained at −20° C., the mixture was sufficiently stirred for 2 hours, and 26.1 ml (8.622 mmol) of 0.33 M CeCl$_3$.2LiCl solution dissolved in THF and 1.182 g (8.622 mmol) of tetramethyl cyclopentenone were added to the mixture under a nitrogen atmosphere. While the temperature was gradually increased to room temperature, the solvents were eliminated by venting. Then, the mixture was titurated using pentane under a nitrogen atmosphere and filtered to obtain a white crystalline powder (41%).

$^1$H NMR (C6D6): δ 1.00 (d, J=6.4 Hz, 3H, Cp-CH$_3$), 1.66-1.74 (m, 2H, quinoline-CH$_2$), 2.64 (t, J=6.0 Hz, 2H, quinoline-CH$_2$), 2.78-2.98 (m, 2H, quinoline-CH$_2$), 3.05 (br s, 1H, Cp-H), 3.76 (br s, 1H, N—H), 6.76 (t, J=7.2 Hz, 1H, quinoline-CH), 6.91 (d, J=5.6 Hz, 1H, quinoline-CH), 6.93 (d, J=7.2 Hz, 1H, quinoline-CH)ppm Example 7

([(1,2,3,4-Tetrahydroquinolin-8-yl)tetramethylcyclopentadienyl-eta5,kapa-N]tit anium dimethyl) compound 220 mg (0.792 mmol) of 2.5 M n-butyllitium (n-BuLi) was gradually added to a cold (−30° C.) solution of 100 mg (0.396 mmol) of the obtained compound in Example 6 dissolved in ether while stirring. The temperature of the mixture was increased to room temperature. The resultant mixture was reacted for 6 hours, filtered, and washed several times with ether. Then the ether was evaporated in vacuum to obtain 90 mg of a pale yellow solid product (dilithium salt compound). It was identified that 0.43 equivalent of ether was coordinated (77%) through $^1$H NMR and $^{13}$C NMR spectroscope.

$^1$H NMR (C6D6): δ 2.03 (br s, 2H, Quinoline-CH$_2$), 2.16 (br s, 12H, Cp-CH$_3$), 3.14 (br s, 2H, Quinoline-CH$_2$), 3.85 (br s, 2H, Quinoline-CH$_2$), 6.33 (t, J=6.4 Hz, 1H, Quinoline-CH), 6.95 (d, J=0.8 Hz, Quinoline-CH), 7.32 (br s, 1H, Quinoline-CH)ppm.

66 mg (0.235 mmol) of TiCl4.DME was mixed with ether at −30□ and the mixture was placed in a refrigerator for about 1 hour. Then, 3 ml (0.470 mmol) of 1.4 M methyllithium (MeLi) was gradually added to the mixture while stirring. After stirring for 15 minutes, 70 mg (0.235 mmol) of dilithium salt compound was added to the mixture. The mixture was reacted for 3 hours while stirring at room temperature. Then the solvent was evaporated in vacuum and the mixture was dissolved in pentane and filtered. The pentane in the resultant mixture was evaporated under a vacuum, and thus 52 mg of dark brown titanium complex was obtained (67%).

$^1$H NMR (C6D6): δ 7.00 (d, J=7.6 Hz, 1H), 9.92 (d, J=7.6 Hz, 1H), 6.83 (t, J=7.6 Hz, 1H), 4.53 (m, 2H), 2.47 (t, J=6.4 Hz, 2H), 2.05 (s, 6H), 1.66 (s, 6H), 1.76-1.65 (m, 2H), 0.58 (s, 6H).

Example 8

5-Indenyl-1,2,3,4-tetrahydroquinoline

Yellow oil was obtained in the same manner as in Example 6, except that indenone was used instead of tetramethyl cyclopentenone and the product was filtered using a column chromatography with a hexane/ethyl acetate (v:v=20:1) solvent (Yield: 49%).

$^1$H NMR (C6D6): δ 1.58-1.64 (m, 2H, quin-CH$_2$), 2.63 (t, J=6.8 Hz, 2H, quin-CH$_2$), 2.72-2.77 (m, 2H, quin-CH$_2$), 3.17 (d, J=2.4 Hz, 2H, indenyl-CH$_2$), 3.85 (br s, 1H, N—H), 6.35 (t, J=2.0 Hz, 1H, indenyl-CH), 6.76 (t, J=7.6 Hz, 1H, quin-CH), 6.98 (d, J=7.2 Hz, 1H, quin-CH), 7.17 (td, J=1.6, 7.2 Hz, 1H, quin-CH), 7.20 (td, J=1.6, 7.2 Hz, 2H, indenyl-CH), 7.34 (d, J=7.2 Hz, 1H, indenyl-CH), 7.45 (dd, J=1.2, 6.8 Hz, 1H, indenyl-CH)ppm. $^{13}$C NMR (C6D6): δ 12.12, 23.08, 27.30, 48.84, 51.01, 119.70, 119.96, 120.95, 126.99, 128.73, 131.67, 136.21 ppm.

Example 9

[(1,2,3,4-Tetrahydroquinolin-8-yl)indenyl-eta5,kapa-N]titanium dimethyl

A dilithium salt compound was obtained in the same manner as in Example 7 using 5-indenyl-1,2,3,4-tetrahydroquinoline (Yield: 95%).

$^1$H NMR (C6D6): δ 2.02 (t, J=4.8 Hz, 2H, quin-CH$_2$), 3.15 (t, J=5.6 Hz, 2H, quin-CH$_2$), 3.94 (br s, 2H, quin-CH$_2$), 6.31 (t, J=7.2 Hz, 1H, indenyl-CH), 6.76-6.83 (m, 2H, quin-CH), 6.99 (t, J=7.2, 2.0 Hz, 2H, quin-CH), 7.48 (d, J=7.2 Hz, 2H, indenyl-CH), 8.02 (t, J=8.0 Hz, 2H, indenyl-CH) ppm.

A titanium compound was prepared using the obtained dilithium salt compound in the same manner as in Example 7 (Yield: 47%).

$^1$H NMR (C6D6): δ −0.01 (s, 3H, Ti—CH$_3$), 0.85 (s, 3H, Ti—CH$_3$), 1.56-1.68 (m, 2H, quin-CH$_2$), 2.43 (t, J=6.4 Hz, 2H, quin-CH$_2$), 6.30 (d, J=3.6 Hz, 1H, indenyl-CH), 6.61 (d, J=3.6 Hz, 1H, indenyl-CH), 6.70 (ddd, J=0.8, 6.8, 8.4 Hz, 1H, indenyl-CH), 6.85 (t, J=7.6 Hz, 1H, quin-CH), 6.95 (tt, J=0.8, 6.8 Hz, 1H, quin-CH), 7.01 (tdd, J=0.8, 6.8, 8.4 Hz, 2H, indenyl-CH), 7.13-7.17 (m, 1H, quin-CH), 7.48 (d, J=8.4 Hz, 1H, indenyl-CH) ppm. $^{13}$C NMR (C6D6): δ 22.83, 27.16, 49.35, 55.12, 58.75, 103.36, 119.63, 120.30, 123.18, 125.26, 125.60, 127.18, 127.36, 127.83, 129.13, 129.56, 135.10, 161.74 ppm.

Example 10

5-Fluorenyl-1,2,3,4-tetrahydroquinoline

A yellow solid compound was obtained in the same manner as in Example 6, except that fluorenone was used instead of tetramethyl cyclopentenone and the product was filtered using a column chromatography with a hexane/ethyl acetate (v:v=20:1) solvent and recrystallized in diethyl ether (Yield: 56%).

$^1$H NMR (C6D6): δ 1.20 (t, J=7.6 Hz, 2H, quin-CH$_2$), 1.71 (s, 1H, xx), 2.29 (s, 2H, quin-CH$_2$), 2.38 (t, J=6.0 Hz, 2H, quin-CH$_2$), 2.64 (s, 1H, quin-CH$_2$), 2.72 (s, 2H, quin-CH$_2$), 2.30 (s, 1H, N—H), 3.82 (s, 0.5H, N—H), 4.81 (s, 1H, quin-CH), 6.42 (d, J=7.2 Hz, 2H, quin-CH), 6.81 (t, J=7.2 Hz, 1H, quin-CH), 6.94 (dd, J=1.2, 7.2 Hz, 1H, quin-CH), 7.10 (d, J=7.6 Hz, 2H, fluorenyl-CH), 7.23 (t, J=7.2 Hz, 2H, fluorenyl-CH), 7.32 (d, J=7.6 Hz, 2H, fluorenyl-CH), 7.42 (d, J=6.8 Hz, 1H, quin-CH), 7.67 (d, J=7.2 Hz, 2H, fluorenyl-CH)ppm.

Example 11

[(1,2,3,4-Tetrahydroquinolin-8-yl)fluorenyl-eta5, kapa-N]titanium dimethyl

A dilithium salt compound was obtained in the same manner as in Example 7 using 5-fluorenyl-1,2,3,4-tetrahydroquinoline (Yield: 94%).

$^1$H NMR (C6D6): δ 2.17 (s, 2H, quin-CH$_2$), 3.29-2.26 (m, 2H, quin-CH$_2$), 4.11 (br s, 2H, quin-CH$_2$), 6.31 (t, J=7.2 Hz, 1H, quin-CH), 6.91 (t, J=7.6 Hz, 2H, fluorenyl-CH), 6.99 (d, J=7.2 Hz, 1H, quin-CH), 7.12 (t, J=6.8 Hz, 2H, fluorenyl-CH), 7.58 (dd, J=1.2, 7.6 Hz, 1H, quin-CH), 8.15 (d, J=8.0 Hz, 2H, fluorenyl-CH), 8.57 (d, J=8.0 Hz, 2H, fluorenyl-CH) ppm.

A titanium compound was prepared using the obtained dilithium salt compound in the same manner as in Example 7 (Yield: 47%).

$^1$H NMR (C6D6): δ 0.14 (s, 6H, Ti—CH$_3$), 1.56-1.68 (m, 2H, quin-CH$_2$), 2.48 (t, J=6.4 Hz, 2H, quin-CH$_2$), 4.18-4.30 (m, 2H, quin-CH$_2$), 6.88-6.96 (m, 3H, CH), 7.04 (d, J=7.6 Hz, 1H, quin-CH), 7.10 (ddd, J=1.2, 6.8, 8.4 Hz, 2H, fluorenyl—CH), 7.17 (dd, J=0.8, 8.4 Hz, 2H, fluorenyl-CH), 7.28 (d, J=7.2 Hz, 1H, quin-CH), 7.94 (dd, J=0.8, 8.4 Hz, 2H, fluorenyl-CH) ppm. $^{13}$C NMR (C6D6): δ 14.54, 22.76, 27.26, 48.58, 59.65, 111.21, 118.69, 118.98 120.17, 123.34, 123.67, 126.16, 126.42, 127.75, 129.29, 129.41, 137.28, 160.63 ppm.

Example 12

7-(2,3,4,5-Tetramethyl-1,3-cyclopentadienyl)indoline

Yellow oil was obtained in the same manner as in Example 6, except that indoline was used instead of 1,2,3,4-tetrahydroquinoline and the product was filtered using a column chromatography with a hexane/ethyl acetate (v:v=20:1) solvent (Yield: 15%).

$^1$H NMR (C6D6): δ 0.99 (d, J=7.6 Hz, 1H, Cp-CH), 1.82 (s, 3H, Cp-CH$_3$), 1.87 (s, 6H, Cp-CH$_3$), 2.68-2.88 (m, 2H, ind-CH$_2$), 2.91-2.99 (m, 1H, Cp-CH), 3.07-3.16 (m, 3H, ind-CH$_2$ N—H), 6.83 (t, J=7.4 Hz, 1H, ind-CH), 6.97 (d, J=7.6 Hz, 1H, ind-CH), 7.19 (d, J=6.8 Hz, 1H, ind-CH) ppm.

Example 13

[(Indolin-7-yl)tetramethylcyclopentadienyl-eta5, kapa-N]titanium dimethyl

A titanium compound was prepared using 7-(2,3,4,5-tetramethyl-1,3-cyclopentadienyl)indoline in the same manner as in Example 7 (Yield: 71%).

¹H NMR (C6D6): δ 0.69 (s, 6H, Ti—CH₃), 1.71 (s, 6H, Cp-CH₃), 2.04 (s, 6H, Cp-CH₃), 2.73 (t, J=8.0 Hz, 2H, ind-CH₂), 4.67 (t, J=8.0 Hz, 2H, ind-CH₂), 6.82 (t, J=7.2 Hz, 1H, ind-CH), 7.00 (t, J=7.2 Hz, 2H, ind-CH) ppm. ¹³C NMR (C6D6): δ 12.06, 12.15, 32.24, 54.98, 56.37, 120.57, 120.64, 121.54, 124.02, 126.52, 126.81, 136.75 ppm.

Example 14

2-Methyl-8-(2,3,4,5-tetramethyl-1,3-cyclopentadienyl)-1,2,3,4-tetrahydroquinoline 2-Methyl-8-(2,3,4,5-tetramethyl-1,3-cyclopentadienyl)-1,2,3,4-tetrahydroquinoline was obtained in the same manner as in Example 6, except that 5.02 g (34.1 mmol) of 1,2,3,4-tetrahydroquinaldine was used instead of 1,2,3,4-tetrahydroquinoline (Yield: 51%).

¹H NMR (CDCl₃): δ 6.89 (d, J=7.2 Hz, 1H, CH), δ 6.74 (d, J=7.2 Hz, 1H, CH), δ 6.57 (t, J=7.4 Hz, 1H, CH), δ 3.76 (br s, 1H, NH), δ 3.45 (br s, 1H, Cp-CH), δ 3.32 (m, 1H, quinoline-CH), δ 3.09-2.70 (m, 2H, quinoline-CH₂), δ 1.91 (s, 3H, Cp-CH₃), δ 1.87 (s, 3H, Cp-CH₃), δ 1.77 (s, 3H, Cp-CH₃), δ 1.67-1.50 (m, 2H, quinoline-CH₂), δ 1.17 (d, J=6.4 Hz, 3H, quinoline-CH₃), δ 0.93 (d, J=7.6 Hz, 3H, Cp-CH₃) ppm.

Example 15

[(2-Methyl-1,2,3,4-tetrahydroquinolin-8-yl)tetramethylcyclopenta-dienyl-eta5,kapa-N]titanium dimethyl 4.92 g of pale yellow solid (dilithium salt compound) to which 1.17 equivalent of diethyl ether was coordinated was obtained in the same manner as in Example 7 using 4.66 g (17.4 mmol) of 2-methyl-8-(2,3,4,5-tetramethyl-1,3-cyclopentadienyl)-1,2,3,4-tetrahydroquinoline (Yield: 77%).

¹H NMR (Pyridine-d8): δ 7.37 (br s, 1H, CH), δ 7.05 (d, J=6 Hz, 1H, CH), δ 6.40 (t, J=6.8 Hz, 1H, CH), δ 3.93 (br s, 1H, CH), δ 3.27 (m, 1H, CH), δ 3.06 (m, 1H, CH), δ 2.28-2.07 (m, 12H, Cp-CH₃), δ 1.99 (m, 1H, CH), δ 1.78 (m, 1H, CH), δ 1.18 (d, J=5.6 Hz, quinoline-CH₃) ppm.

0.56 g of a titanium compound was prepared in the same manner as in Example 7 using 1.00 g (2.73 mmol) of the obtained dilithium salt compound (Yield 60%).

¹H NMR (CDCl₃): δ 6.95 (d, J=8 Hz, 1H, CH), δ 6.91 (d, J=8 Hz, 1H, CH), δ 6.73 (t, J=8 Hz, 1H, CH), δ 5.57 (m, 1H, CH), δ 2.83 (m, 1H, CH), δ 2.55 (m, 1H, CH), δ 2.24 (s, 3H, Cp-CH₃), δ 2.20 (s, 3H, Cp-CH₃), δ 1.94-1.89 (m, 1H, CH), δ 1.83-1.75 (m, 1H, CH), δ 1.70 (s, 3H, Cp-CH₃), δ 1.60 (s, 3H, Cp-CH₃), δ 1.22 (d, J=6.8 Hz, 3H, quinoline-CH₃), δ 0.26 (d, J=6.8 Hz, 6H, TiMe₂-CH₃) ppm.

Example 16

6-Methyl-8-(2,3,4,5-tetramethyl-1,3-cyclopentadienyl)-1,2,3,4-tetrahydroquinoline 6-Methyl-8-(2,3,4,5-tetramethyl-1,3-cyclopentadienyl)-1,2,3,4-tetrahydroquinoline was obtained in the same manner as in Example 6 except that 5.21 g (35.4 mmol) of 6-methyl-1,2,3,4-tetrahydroquinoline was used instead of 1,2,3,4-tetrahydroquinoline (Yield: 34%).

¹H NMR (CDCl₃): δ 6.70 (s, 1H, CH), δ 6.54 (s, 1H, CH), δ 3.71 (br s, 1H, NH), δ 3.25-3.05 (m, 3H, Cp-CH, quinoline-CH₂), δ 2.76 (t, J=6.4 Hz, 2H, quinoline-CH₂), δ 2.19 (s, 3H, CH₃), δ 1.93-1.86 (m, 2H, quinoline-CH₂), δ 1.88 (s, 3H, Cp-CH₃), δ 1.84 (s, 3H, Cp-CH₃), δ 1.74 (s, 3H, Cp-CH₃), δ 0.94 (br d, J=6.8 Hz, 3H, Cp-CH₃) ppm.

Example 17

[(6-Methyl-1,2,3,4-tetrahydroquinolin-8-yl)tetramethylcyclopenta-dienyl-eta5,kapa-N]titanium dimethyl 2.56 g of pale yellow solid (dilithium salt compound) to which 1.15 equivalent of diethyl ether was coordinated was obtained in the same manner as in Example 7 using 3.23 g (12.1 mmol) of 6-methyl-8-(2,3,4,5-tetramethyl-1,3-cyclopentadienyl)-1,2,3,4-tetrahydroquinoline (Yield: 58%).

¹H NMR (Pyridine-d8): δ 7.02 (br s, 1H, CH), δ 6.81 (s, 1H, CH), δ 3.94 (m, 2H, CH₂), δ 3.19 (m, 2H, CH₂), δ 2.52-2.10 (m, 17H, CH₂, quinoline-CH₃, Cp-CH₃) ppm.

0.817 g of a titanium compound (58%) was prepared in the same manner as in Example 7 using 1.50 g (4.12 mmol) of the obtained dilithium salt compound.

¹H NMR (C₆D₆): δ 6.87 (s, 1H, CH), δ 6.72 (s, 1H, CH), δ 4.57 (m, 2H, CH₂), δ 2.45 (t, J=6.2 Hz, 2H, CH₂), δ 2.24 (s, 3H, quinoline-CH₃), δ 2.05 (s, 6H, Cp-CH₃), δ 1.72-1.66 (m, 2H, CH₂), δ 1.69 (s, 6H, Cp-CH₃), δ 0.57 (s, 6H, TiMe₂-CH₃) ppm.

Example 18

2-Methyl-7-(2,3,4,5-tetramethyl-1,3-cyclopentadienyl)indoline

2-Methyl-7-(2,3,4,5-tetramethyl-1,3-cyclopentadienyl)indoline was obtained in the same manner as in Example 6, except that 6.23 g (46.8 mmol) of 2-methylindoline was used instead of 1,2,3,4-tetrahydroquinoline (Yield: 19%).

¹H NMR (CDCl₃): δ 6.97 (d, J=7.2 Hz, 1H, CH), δ 6.78 (d, J=8 Hz, 1H, CH), δ 6.67 (t, J=7.4 Hz, 1H, CH), δ 3.94 (m, 1H, quinoline-CH), δ 3.51 (br s, 1H, NH), δ 3.24-3.08 (m, 2H, quinoline-CH₂, Cp-CH), δ 2.65 (m, 1H, quinoline-CH₂), δ 1.89 (s, 3H, Cp-CH₃), δ 1.84 (s, 3H, Cp-CH₃), δ 1.82 (s, 3H, Cp-CH₃), δ 1.13 (d, J=6 Hz, 3H, quinoline-CH₃), δ 0.93 (3H, Cp-CH₃) ppm.

Example 19

[(2-Methylindolin-7-yl)tetramethylcyclopentadienyl-eta5,kapa-N]titanium dimethyl A dilithium salt compound to which 0.58 equivalent of diethyl ether was coordinated was obtained in the same manner as in Example 7 using 2.25 g (8.88 mmol) of 2-methyl-7-(2,3,4,5-tetramethyl-1,3-cyclopentadienyl)-indoline (1.37 g, Yield: 50%).

¹H NMR (Pyridine-d8): δ 7.22 (br s, 1H, CH), δ 7.18 (d, J=6 Hz, 1H, CH), δ 6.32 (t, 1H, CH), δ 4.61 (br s, 1H, CH), δ 3.54 (m, 1H, CH), δ 3.00 (m, 1H, CH), δ 2.35-2.12 (m, 13H, CH, Cp-CH₃), δ 1.39 (d, indoline-CH₃) ppm.

A titanium compound was prepared using 1.37 g (4.44 mmol) of the obtained dilithium salt compound in the same manner as in Example 7.

¹H NMR (C₆D₆): δ 7.01-6.96 (m, 2H, CH), δ 6.82 (t, J=7.4 Hz, 1H, CH), δ 4.96 (m, 1H, CH), δ 2.88 (m, 1H, CH), δ 2.40 (m, 1H, CH), δ 2.02 (s, 3H, Cp-CH₃), δ 2.01 (s, 3H, Cp-CH₃), δ 1.70 (s, 3H, Cp-CH₃), δ 1.69 (s, 3H, Cp-CH₃), δ 1.65 (d, J=6.4 Hz, 3H, indoline-CH₃), δ 0.71 (d, J=10 Hz, 6H, TiMe₂-CH₃) ppm.

Comparative Example 1

Dimethylsilyl(t-butylamido)(tetramethylcyclopentadienyl)titanium dichloride

Dimethylsilyl(t-butylamido)(tetramethylcyclopentadienyl)titanium dichloride was purchased from Boulder Scientific, Inc. (U.S.A.) and directly used for the ethylene copolymerization.

Ethylene Copolymer

Example 20

Copolymerization of Low-Pressure Ethylene and 1-hexene 30 ml of toluene and 0.3 M 1-hexene was added to a 250 ml Endrew reactor, and the reactor was preheated to a temperature of 90° C. 0.5 µmol of titanium transition metal complex prepared in Example 5 treated with 200 µmol of triisobutylaluminum compound and 2 µmol of trityl tetrakis(pentafluorophenyl)borate cocatalyst were sequentially added to the reactor. Then copolymerization was performed for 5 minutes, and then 4 bar of ethylene pressure was added to the catalyst tank. The remaining ethylene was eliminated and the polymer solution was added to excess ethanol to induce a precipitation. The obtained polymer was washed with ethanol and acetone two to three times, respectively, and the resultant was dried at 80° C. for over 12 hours in a conventional oven.

Example 21

Copolymerization of high-pressure ethylene and 1-butene 1.0 L of hexane solvent and an appropriate amount of 1-butene comonomer was added to a 2 L autoclave reactor. The reactor was heated to 90° C., and the reactor was filled with 20 bar of ethylene. 2 µmol of titanium transition metal complex prepared in Example 5 treated with 100 µmol of triisobutylaluminum compound and 10 µmol of dimethylanilinium tetrakis(pentafluorophenyl)borate cocatalyst were sequentially added to a catalyst injecting cylinder and injected into the reactor. Polymerization was performed for 10 minutes by continuously injecting ethylene in order to maintain the pressure of the reactor between 19 bar to 20 bar. Heat generated from the reaction was removed through cooling coil installed in the reactor and the temperature was maintained as constant as possible. After the polymerization, the polymer solution was discharged to the lower portion of the reactor and cooled using excess ethanol. The obtained polymer was dried for over 12 hours in a conventional oven.

Example 22

Copolymerization of High-Pressure Ethylene and 1-octene 1.0 L of hexane solvent and an appropriate amount of 1-octene was added to a 2 L autoclave reactor. The reactor was preheated to 160° C., and was filled with ethylene at a pressure of 28 bar. 5.0 µmol of titanium transition metal complex prepared in Example 5 treated with 1.25 µmol of triisobutylaluminum compound and 25 µmol of trityl tetrakis(pentafluorophenyl)borate cocatalyst were sequentially added to a 25 ml catalyst storing tank and filled. Polymerization was performed for 10 minutes while 40 bar of ethylene was added to the catalyst tank. The remaining ethylene was eliminated and the polymer solution was added to excess ethanol to induce a precipitation. The obtained polymer was washed with ethanol and acetone two to three times, respectively, and the resultant was dried at 80° C. for over 12 hours in a conventional oven.

Example 23

Copolymerization of High-Pressure Ethylene and 1-butene 1.0 L of hexane solvent and an appropriate amount of 1-butene comonomer was added to a 2 L autoclave reactor. The reactor was heated to 150° C., and the reactor was filled with 35 bar of ethylene. 1.0 µmol (Al/Ti=25) of titanium transition metal complex treated with an appropriate amount of triisobutylaluminum compound and dimethylanilinium tetrakis(pentafluorophenyl)borate cocatalyst (B/Ti=5) were sequentially added to a catalyst injecting cylinder and injected into the reactor. Polymerization was performed for 10 minutes by continuously injecting ethylene in order to maintain the pressure of the reactor between 34 bar to 35 bar. Heat generated from the reaction was removed through cooling coil installed in the reactor and the temperature was maintained as constant as possible. After the polymerization, the polymer solution was discharged to the lower portion of the reactor and cooled using excess ethanol. The obtained polymer was dried for over 12 hours in a conventional oven.

Comparative Example 2

Polymerization was performed in the same manner as in Example 20, except that the transition metal complex prepared in Comparative Example 1 was used instead of the transition metal complex prepared in Example 5.

Comparative Example 3

Polymerization was performed in the same manner as in Example 21, except that the transition metal complex prepared in Comparative Example 1 was used instead of the transition metal complex prepared in Example 5.

Comparative Example 4

Polymerization was performed in the same manner as in Example 22, except that the transition metal complex prepared in Comparative Example 1 was used instead of the transition metal complex prepared in Example 5.

Comparative Example 5

Polymerization was performed in the same manner as in Example 23, except that the transition metal complex prepared in Comparative Example 1 was used instead of the transition metal complex prepared in Example 5.

Properties Measurement (Weight, Activity, Melt Index, Melting Point, and Density)

A Melt Index (MI) of the polymers produced in Examples 1-10 and Comparative Examples 1-4 was measured using a ASTM D-1238 (Conditions: E, 190° C., 2.16 Kg load). A melting point ($T_m$) of the polymers was measured using a Differential Scanning Calorimeter (DSC) 2920 produced by TA Inc. That is, the temperature was increased to 200° C., maintained at 200° C. for 5 minutes, and decreased to 30° C. Then the temperature was increased again and the summit of the DSC curve was measured as the melting point. The temperature was increased and decreased by 10° C./min, and the melting point was obtained in a second temperature increase period.

In order to measure the density of the polymers, a sample that had been treated with 1,000 ppm of an antioxidant was formed into a sheet having a thickness of 3 mm and a radius of 2 cm by a 180° C. press mold, and then the prepared sheet was cooled by 10° C./min. The cooled sheet was measured using a Mettler scale.

Experimental Example 1

The properties of the copolymers prepared in Example 20 and Comparative Example 2 respectively using the transition metal complexes prepared in Example 5 and Comparative Example 1 were measured according to the experimental methods described above. The results are presented in Table 1.

TABLE 1

Results of copolymerization of ethylene and 1-hexene

|  | Catalyst | 1-hexene (M) | Activity (Kg/mmol-Ti hr) | Molecular weight[a] | Branch content (mol %) |
|---|---|---|---|---|---|
| Example 20 | Example 5 | 0.3 | 21 | 81,000 | 24 |
| Comparative Example 2 | Comparative Example 1 | 0.3 | 12 | 113,000 | 15 |

[a] weight average molecular weight (Mw)

As shown in Table 1, a degree of copolymerization activity of catalyst of Example 5 of the present invention was higher compared to Comparative Example 1. The molecular weight of the copolymer of Example 20 was relatively small; however, the Branch content was very high, and thus it shows that the reactivity of catalyst of Example 5 for the olefin monomer having large steric hindrance such as 1-hexene is excellent.

Experimental Example 2

The properties of the copolymers prepared in Example 21 and Comparative Example 3 respectively using the transition metal complexes prepared in Example 5 and Comparative Example 1 were measured according to the experimental methods. The results are presented in Table 2. According to the content of 1-butene, Example 9 was divided to Examples 21A and 21B.

TABLE 2

Results of copolymerization of ethylene and 1-butene

|  | Catalyst | 1-Butene (M) | Activity (Kg/mmol-Ti hr) | Melt index[a] (g/10 min) | Melt index[b] (g/10 min) | Density (g/cc) |
|---|---|---|---|---|---|---|
| Example 21A | Example 5 | 0.8 | 216.0 | 0 | 3.62 | 0.864 |
| Example 21B | Example 5 | 1.2 | 280.2 | 1 | 27 | 0.857 |
| Comparative Example 3 | Comparative Example 1 | 1.2 | 340.5 | 3.10 | ∞ | 0.878 |

[a] $I_2$ value,
[b] $I_{21.6}$ value

As shown in Table 2, the catalyst of Example 5 of the present invention had a lower copolymerization activity than that of Comparative Example 1 when ethylene was copolymerized with 1-butene. However, the molecular weight of the copolymer of Examples 21A and 21B was higher than that of Comparative Example 3. According to an embodiment of the present invention, the reactivity of catalyst of Example 5 for the olefin monomer having large steric hindrance such as 1-butene was relatively excellent since the density of the copolymer was very low. In particular, in Example 21A, even though a smaller amount of 1-butene (0.8 M) was used, a polymer having lower density than Comparative Example 3 using 1.2 M 1-butene was obtained. Therefore, the catalyst according to an embodiment of the present invention showed excellent copolymerization reactivity.

Experimental Example 3

The properties of the copolymers prepared in Example 22 and Comparative Example 4 respectively using the transition metal complexes prepared in Example 5 and Comparative Example 1 were measured according to the experimental methods descried above. The results are presented in Table 3. According to the content of 1-octene, Example 22 was divided to Examples 22A and 22B.

TABLE 3

Results of copolymerization of ethylene and 1-octene

|  | Catalyst | Temperature (° C.) | 1-octene (M) | Activity (Kg/mmol-Ti hr) | Melt index[a] (g/10 min) | Melting point | Density (g/cc) |
|---|---|---|---|---|---|---|---|
| Example 22A | Example 5 | 160 | 0.6 | 48.0 | 6.4 | 58.6 | 0.869 |
| Example 22B | Example 5 | 160 | 0.8 | 55.6 | 5.3 | 49.8 | 0.864 |
| Comparative Example 4 | Comparative Example 1 | 160 | 0.8 | 30.4 | 5.1 | 98.2 | 0.904 |

[a] $I_2$ value

As shown in Table 3, the catalyst of Example 5 of the present invention had a higher copolymerization activity than that of Comparative Example 1 when ethylene was copolymerized with 1-octene. The molecular weight of the copolymer of Examples 22A and 22B was similar to that of Comparative Example 4. The reactivity of the catalyst of Example 5 for the olefin monomer having large steric hindrance such as 1-octene was relatively excellent since the melting point and density of the copolymer was low. In particular, in the present invention, even though a smaller amount of 1-octene (0.6 M) was used, a polymer having lower density than Comparative Example 4 using 0.8 M 1-octene was obtained. Therefore, the catalyst composition according to an embodiment of the present invention showed excellent copolymerization reactivity at a high temperature such as 160° C.

Experimental Example 4

The properties of the copolymers prepared in Example 23 and Comparative Example 5 respectively using the transition metal complexes prepared in Examples 7, 9, 11, 13, 15, 17, 19 and 2 and Comparative Example 1 were measured according to the experimental methods. The results are presented in Table 4.

TABLE 4

Results of copolymerization of ethylene and 1-butene

| | | 1-Butene (M) | Activity (kg/mmol-Ti) | Melt index[a] (g/10 min) | Melt index[b] (g/10 min) | Density (g/cc) |
|---|---|---|---|---|---|---|
| Example 23A | Example 7 | 1.6 | 43.7 | 3.5 | 28.8 | 0.859 |
| Example 23B | Example 9 | 1.6 | 3.4 | 0 | 0 | 0.870 |
| Example 23C | Example 11 | 1.6 | 16.6 | 0 | 0 | 0.860 |
| Example 23D | Example 13 | 1.6 | 15.3 | 0 | 0.66 | 0.873 |
| Example 23E | Example 15 | 1.6 | 36.0 | 15.4 | ∞ | 0.862 |
| Example 23F | Example 17 | 1.6 | 29.8 | 1.3 | 12.5 | 0.860 |
| Example 23G | Example 19 | 1.6 | 22.1 | 0 | 0.8 | 0.873 |
| Comparative Example 5A | Comparative Example 1 | 1.6 | 30.5 | 5.9 | 59 | 0.900 |
| Example 23H | Example 2[c] | 1.2 | 57.5 | 0 | 1.3 | 0.881 |
| Comparative Example 5B | Comparative Example 1[c] | 1.2 | 44.1 | 0 | 1.2 | 0.902 |

[a]$I_2$ value,
[b]$I_{21.6}$ value,
[c]120° C. polymerization

As shown in Table 4, the catalyst of the present invention had relatively enhanced reactivity for the olefin monomer having large steric hindrance such as 1-butene since the molecular weight of the copolymer of Example 23 (23A~23H) was higher than that of Comparative Example 5 (5A~5B) and the density of the copolymer was lower than that of Comparative Example 5 (5A~5B) when 1-butene was applied. Particularly, the catalyst compounds obtained in Examples 7, 15, and 17 had a similar or higher polymerization activity compared to catalyst compounds obtained in Comparative Example 1, and even at 120° C., the catalyst compounds obtained in Example 2 showed a higher polymerization activity, a higher molecular weight, and a lower copolymer density compared to catalyst compounds obtained in Comparative Example 1 Therefore, the catalyst according to the present invention showed excellent polymerization reactivity.

Accordingly, the transition metal complex and the catalyst composition of the present invention including the transition metal complex had improved copolymerization reactivity in α-olefin polymerization compared to a conventional catalyst composition. Therefore, when the catalyst composition of the present invention was used in α-olefin copolymerization, a copolymer having lower density can be obtained. Therefore, when the catalyst composition of the present invention is used, a copolymer with a higher amount of α-olefin than the conventional catalyst composition can be obtained.

A transition metal complex of the present invention has a pentagon ring structure having an amido group connected by a phenylene bridge in which a stable bond is formed in the vicinity of the metal site, and thus, a sterically hindered monomer can easily approach the transition metal complex. By using a catalyst composition including the transition metal complex according to the present invention, a linear low density polyolefin copolymer having a high molecular weight and a very low density polyolefin copolymer having a density of 0.910 g/cc or less can be produced in a polymerization of monomers having large steric hindrance. Further, the reactivity for the olefin monomer having large steric hindrance is excellent.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An amine-based compound represented by Formulae 3 and 4 below:

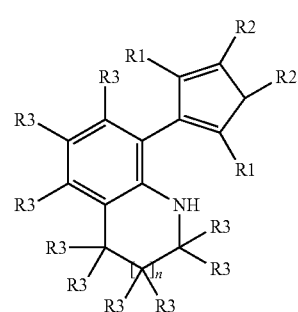

Formula 3

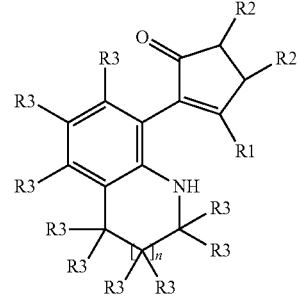

Formula 4 where, $R_1$s and $R_2$s are each independently one selected from the group consisting of: a hydrogen atom, a $C_{1-20}$ alkyl radical, a $C_{6-20}$ aryl radical, a silyl radical, a $C_{2-20}$ alkenyl radical, a $C_{7-20}$ alkylaryl radical, a $C_{7-20}$ arylalkyl radical, and a metalloid radical of Group 14 substituted with a $C_{1-20}$ hydrocarbyl, wherein $R_1$ and $R_2$ can be connected to each other by an alkylidene radical containing a $C_{1-20}$ alkyl or aryl radical to form a ring;

each of the $R_3$s are independently one selected from the group consisting of: a hydrogen atom, a halogen radical, a $C_{1-20}$ alkyl radical, a $C_{6-20}$ aryl radical, a $C_{1-20}$ alkoxy radical, a $C_{6-20}$ aryloxy radical, and an amido radical, wherein at least two $R_3$s can be connected to each other to form an aliphatic or aromatic ring;

n is a integer such as 0 or 1.

* * * * *